US008003400B2

(12) United States Patent
Kobold et al.

(10) Patent No.: US 8,003,400 B2
(45) Date of Patent: Aug. 23, 2011

(54) MEASUREMENT OF VITAMIN D

(75) Inventors: Uwe Kobold, Weilheim (DE); Thomas Duelffer, Weilheim (DE); Michael Grol, Feldafing (DE); Rupert Herrmann, Weilheim (DE); Herbert Von der Eltz, Weilheim (DE); Leopold Von Proff, Hohenpeissenberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 12/326,972

(22) Filed: Dec. 3, 2008

(65) Prior Publication Data

US 2010/0285603 A1 Nov. 11, 2010

Related U.S. Application Data

(63) Continuation of application No. PCT/EP2007/004924, filed on Jun. 4, 2007.

(30) Foreign Application Priority Data

Jun. 6, 2006 (EP) .................................... 06011605

(51) Int. Cl.
*G01N 33/00* (2006.01)
(52) U.S. Cl. ........... 436/131; 436/127; 422/430; 422/50
(58) Field of Classification Search .................. 436/131, 436/127; 422/61, 50
See application file for complete search history.

(56) References Cited

U.S. PATENT DOCUMENTS

| 5,981,779 A | 11/1999 | Holick et al. |
| 2004/0096900 A1 | 5/2004 | Laurie et al. |
| 2004/0132104 A1 | 7/2004 | Sackrison et al. |

FOREIGN PATENT DOCUMENTS

| EP | 0753743 | 1/1994 |
| WO | 9967211 A1 | 12/1999 |
| WO | 0246746 A2 | 6/2002 |
| WO | 0257797 A2 | 7/2002 |

OTHER PUBLICATIONS

Vissers J.P.C., Recent developments in microcolumn liquid chromatography, 1999, Journal of Chromatography A, 856, pp. 117-143.*
Park S. et al., Ionic Liquids Create New Opportunities for Nonaqueous Biocatalysis with Polar Substrates: Acylation of Glucose and Ascorbic Acid, 2003, American Chemical Society, pp. 225-238.*
Bouillon, R. et al., "Two Direct (Nonchromatographic) Assays for 25-Hydroxyvitamin D," Clin. Chem. 30:11 (1984) 1731-1736.
Holmberg, I. et al "Determination of 25-hydroxyvitamin D3 in Serum by High Performance Liquid Chromatography and Isotope Dilution-Mass Spectrometry," Scand. J. Clin. Lab. Invets, 44 (1984) 275-282.
Shimada, K. et al., "Gas Chromatography and High-Performance Liquid Chromatography of Natural Steroids," Journal of Chromatography A 935 (2001) 141-172.
Vogeser, M. et al., "Candidate Reference Method for the Quantification of Circulationg 25-Hydroxyvitamin D3 by Liquid Chromatography-Tandem Mass Spectrometry," Clinical Chemistry 50:8 (2004) 1415-1417.
Zerwekh, J. et al., "The Measurement of Vitamin D: Analytical Aspects," Ann Clin Biochem 41 (2004) 272-281.

* cited by examiner

*Primary Examiner* — Walter D Griffin
*Assistant Examiner* — Christine T Mui
(74) *Attorney, Agent, or Firm* — Dinsmore & Shohl LLP

(57) ABSTRACT

The present invention relates to a method of measuring a vitamin D metabolite in a sample, the method comprising the steps of (a) treating said sample with a vitamin D metabolite releasing reagent under conditions appropriate to release a vitamin D metabolite from vitamin D-binding protein and not to cause protein precipitation, (b) subjecting the treated sample obtained in step (a) to a chromatographic separation, and (c) measuring a vitamin D metabolite during or after said chromatographic separation. The present invention also relates to methods for determining the vitamin D status of a subject, for use in the diagnosis of disease, and to agents and kits for use in performing the methods of the invention.

9 Claims, 8 Drawing Sheets

MEASUREMENT OF VITAMIN D

RELATED APPLICATIONS

This application is a continuation of PCT/EP2007/004924 filed Jun. 4, 2007 and claims priority to EP 06011605.0 filed Jun. 6, 2006.

FIELD OF THE INVENTION

The present invention relates to a method of measuring a vitamin D metabolite in a sample, the method comprising the steps of (a) treating said sample with a vitamin D metabolite releasing reagent under conditions appropriate to release a vitamin D metabolite from vitamin D-binding protein and not to cause protein precipitation, (b) subjecting the treated sample obtained in step (a) to a chromatographic separation, and (c) measuring a vitamin D metabolite during or after said chromatographic separation. The present invention also relates to methods for determining the vitamin D status of a subject, for use in the diagnosis of disease, and to agents and kits for use in performing the methods of the invention.

BACKGROUND OF THE INVENTION

As the term vitamin indicates, a sufficient up-take of vitamin D is pivotal. The level of circulating vitamin D or vitamin D metabolites in a subject is referred to as vitamin D status. Malnutrition with regard to vitamin D is an important factor in the cause of a number of diseases including rickets in children and osteomalacia and may be even osteoporosis in adults. Knowledge of the vitamin D status by measurement of Vitamin D and its metabolites in a clinical sample is very helpful in the assessment of a patient and may by of help to the clinician in establishing a diagnosis. Not surprisingly, there has been a steady increase in the effort towards improving methods for the measurement of vitamin D and its metabolites in body fluids.

In our nutrition vitamin D is available in two forms, i.e., either as vitamin $D_2$ or as vitamin $D_3$. Vitamin $D_2$ is produced outside the body by irradiation of ergosterol from yeast and fungi, and is found in a human being when taken up in the form of fortified foods or pharmaceutical preparations. Vitamin $D_3$, on the other hand, is formed in animals from 7-dehydrocholesterol upon exposure to ultraviolet light. This reaction occurs in the skin. Vitamin $D_3$ is also available in the diet, for example from fish liver oils.

Nutritional vitamin D, in the form of vitamin $D_2$ or $D_3$, after its up-take into the human body is rapidly converted to the circulating metabolite, 25-hydroxyvitamin D, which is found outside cells, tightly bound to circulating vitamin D binding protein.

Due to the rapid conversion of vitamin D to its first metabolite, 25-hydroxyvitamin D, measurement of vitamin D does not give a useful indication of the vitamin D status of a subject. Other metabolites of vitamin D, such as 1α,25-dihydroxyvitamin D, circulate at a concentration 1000 times lower than non-1α-hydroxylated metabolites such as 25-hydroxyvitamin D, and so do not contribute significantly to the estimation of total circulating vitamin D metabolite. For this reason, the 1α-hydroxylated metabolites do not provide a direct or useful indication of vitamin D status. 25-hydroxyvitamin D is the metabolite with the highest serum concentration, and is easy to measure. It has therefore become the most common marker of vitamin D status in a subject.

Vitamin D metabolites also bind to other serum proteins, e.g., to albumin, however, much less tightly than to the binding protein. It is generally accepted that methods facilitating the release of vitamin D out of a vitamin D-vitamin D binding protein complex, will also be appropriate to set it free out of the other less strong complexes as well. The rapid and strong binding of various vitamin D metabolites to vitamin D binding protein thus is the major concern in detection of a vitamin D metabolite and enormously hampers the measurement. All presently known methods require that vitamin D metabolites have to be released from vitamin D binding protein. In such procedures vitamin D binding protein usually is denatured. This typically also requires an extraction step which separates vitamin D binding protein along with other denatured proteins from the vitamin D metabolite of interest and removes the denatured protein fraction from the sample. This way the vitamin D metabolites of interest become available in a separate fraction and is more easily handled and detected.

Extraction has been achieved by a number of methods, including solvent based extraction by adding to the sample an organic solvent such as chloroform, hexane or ethyl acetate and hexane. The organic and aqueous layers are separated and the solvent evaporated. The residue is then reconstituted in a water miscible solvent such as ethanol. Reverse phase cartridge extraction methods have also been used. Other traditional methods include the use of HPLC and mass spectroscopy to achieve separation of individual vitamin D metabolites and exclude from the sample interfering factors such as binding proteins.

Armbruster, F. P., et al. (WO 99/67211) teach that a serum or plasma sample may be treated by ethanol in order to release a vitamin D metabolite out of its complex with vitamin D binding protein. The precipitated protein is spun down and a vitamin D metabolite is obtained in the supernatant. The vitamin D metabolite comprised in such supernatant can be easily detected, e.g., by any liquid chromatography based method.

An alternative solution is proposed in EP 0 753 743, Salts of periodates are recommended to achieve release of a vitamin D metabolite from vitamin D binding protein. Like usual the precipitate comprising vitamin D binding protein is removed by centrifugation and the supernatant is used in the detection of a vitamin D metabolite of interest.

A "Candidate reference method for the quantification of circulating 25-hydroxyvitamin D3 by liquid chromatography-tandem mass spectrometry" has recently been introduced by Vogeser, M. et al., Clin. Chem. 50 (2004) 1415-1417. For exact quantification the use of a stable-isotope-labeled 25-hydroxyvitamin D3 is proposed. This isotope-labeled internal standard co-purifies with natural 25-hydroxyvitamin D3 and by determining this internal standard it is possible to compensate for variations in the extraction and/or detection process. Like for most routine procedures used in measurement of a vitamin D metabolite the method described by Vogeser et al. is based on an acetonitrile extraction step.

Bouillon R. et al., Clin Chem 30 (1984) 1731-1736, describe two "direct" assays for 25-hydroxyvitamin D. Whilst the assays described do not require a chromatography step—as required in more traditional methods—they still require extraction of the vitamin D from vitamin D binding proteins by the use of solvent precipitation.

Holick, M. F. and Ray, R. (U.S. Pat. No. 5,981,779) describe methods for assaying vitamin D and its metabolites. Their procedure is based on a competitive binding assay using a purified vitamin D binding protein as the specific binding agent. A prerequisite for this assay also is that a vitamin D metabolite of interest has first to be isolated from the sample, separated from its binding protein and only thereafter may be measured.

In the measurement of certain steroid hormones from serum, plasma or other biological fluids steroid analogues are used to displace these hormones from their binding proteins. These steroid analogues must bind to the relevant steroid binding proteins, and at the same time must not cross react with the antibody used in the immunoassay. The steroid analogue saturates the steroid binding protein, displacing the steroid and allowing the steroid to bind to the antibodies of the immunoassay.

In theory the use of a (specific) competitive displacer such as a vitamin D analogue that does not cross-react with the assay antibody, should be able to provide a "direct assay" (by analogy to direct steroid measurement methods). However, since the concentration of DBP is very high in serum samples it would have to be expected that very high concentrations of such vitamin D analogue would be required.

Recently, Laurie et al. (US 2004/0096900) have shown that 8-anilino-1-naphthalenesulfonic acid may be used to displace a vitamin D metabolite from vitamin D binding protein. The vitamin metabolite is then measured by a competitive enzyme immuno assay.

Other immunological assay procedures for detection of certain vitamin D metabolites (cf., e.g., WO 02/57797 and US 2004/0132104) have to meet a delicate balance: On the one hand a vitamin D metabolite has to be released as efficiently as possible from its binding protein; on the other hands the reagents used for such release must not interfere with the immunoassay procedure. It appears that these procedures have to somehow compromise in between these two requirements. It has been found and shown that the immunological vitamin D assays available so far suffer from quite a few draw-backs as described, e.g., by Zerwekh, J. E., Ann. Clin. Biochem. 41 (2004) 272-281).

Immunoassays are rather complicated and require a lot of specific reagents and in most cases also machines to produce a clinically relevant result. Chromatographic separation procedures on the contrary are far less demanding in terms of the reagents needed. Currently must routine procedures for measurement of a vitamin D metabolite rely upon at least one extraction step followed by at least one chromatographic separation step. Such chromatographic separation usually is then directly followed by an appropriate detection step. It would represent a significant improvement in clinical routine if a vitamin D metabolite of interest could be released efficiently from its binding protein whereby the same method is not causing a negative impact on other sample constituents, e.g., no precipitation of proteins and thereafter be measured without any manual handling step, e.g., not requiring an extraction step and/or not requiring a centrifugation step.

The present invention helps to overcome or to at least ameliorate some of the problems associated with the prior art procedures, by providing a method for measuring a vitamin D metabolite present in a sample, whereby the improved method is easily combined and based on a standard liquid chromatography procedure, and does not require any manual handling.

SUMMARY OF THE INVENTION

The present invention relates to a method of measuring a vitamin D metabolite in a sample, the method comprising the steps of (a) treating said sample with a vitamin D releasing reagent under conditions appropriate to release a vitamin D metabolite from vitamin D-binding protein and not to cause protein precipitation, (b) subjecting the treated sample obtained in step (a) to a chromatographic separation, and (c) measuring a vitamin D metabolite during or after said chromatographic separation.

Thus, the present invention satisfies the pressing need for a simple yet effective method for measuring a vitamin D metabolite of interest in a serum or plasma sample. It is based upon the surprising discovery of an appropriate vitamin D releasing reagent that enables release and direct online chromatographic separation of a vitamin D metabolite from vitamin D binding protein. This way the amount of a vitamin D metabolite can be detected or measured, without requiring its extraction from the sample. In essence, the invention discloses for the first time that appropriate vitamin D releasing reagents may eliminate the need of an extraction step in the online detection of vitamin D. In addition a method based on the use of the novel and appropriate vitamin D releasing reagent is suited to routine use in clinical biochemical laboratories.

DETAILED DESCRIPTION OF THE INVENTION

Figure 1:
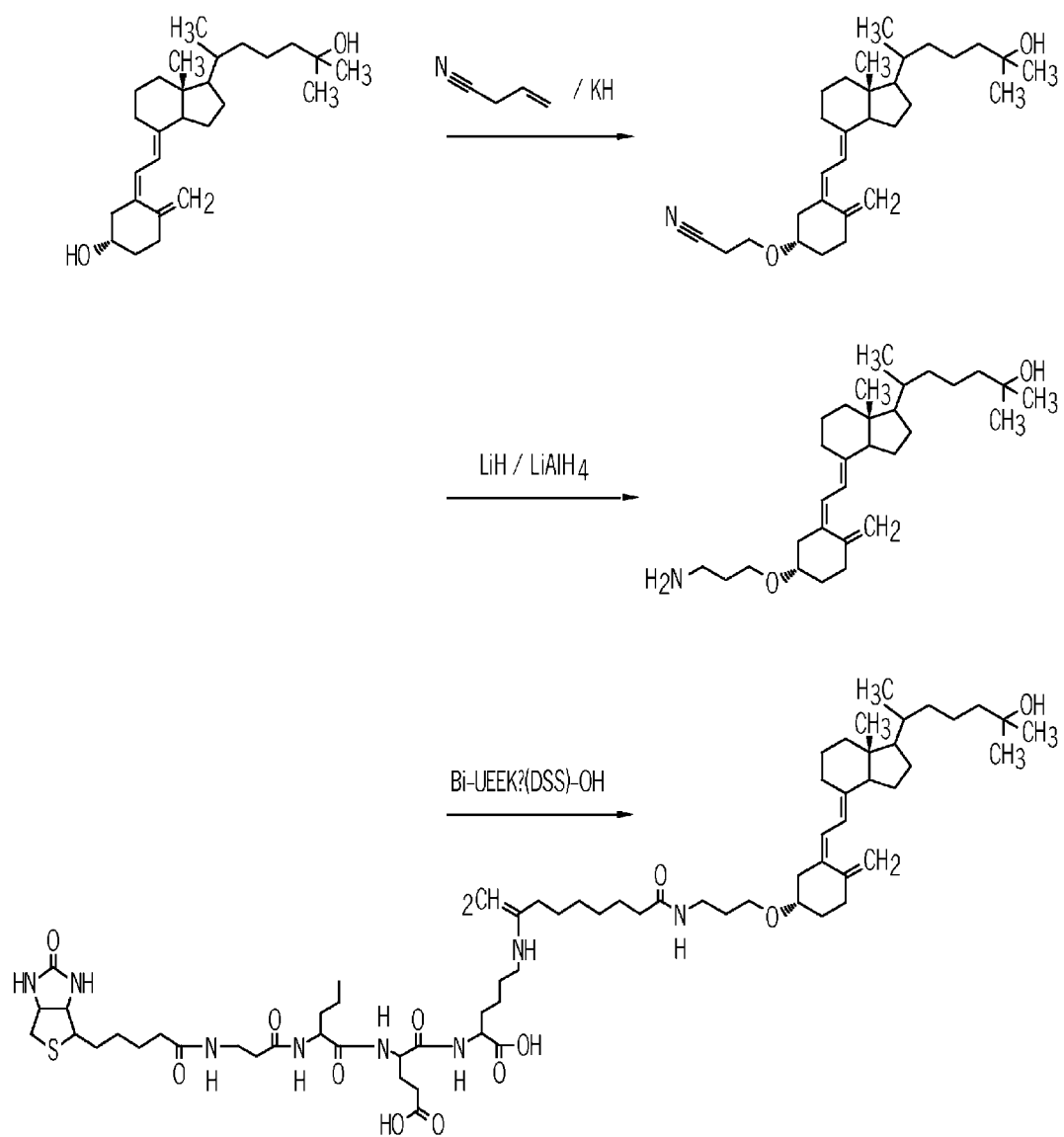
FIG. 1: Synthesis of biotinylated 25-hydroxyvitamin $D_3$. The steps used in the synthesis of a biotin-25-hydroxyvitamin $D_3$-conjugate are depicted schematically.

The present invention may be performed on any sample of plasma or serum, preferably from an individual. The individual whose plasma or serum is to be analyzed may be one for whom it is desirable to determine vitamin D status. Measuring a vitamin D metabolite of interest present in a sample of plasma or serum may include both qualitative as well as quantitative measurements, i.e., detecting the presence of a vitamin D metabolite of interest in the sample, or determining the amount of a vitamin D metabolite present, respectively. Preferably the amount of a vitamin D metabolite of interest is compared with a key detailing whether the amount measured represents a deficiency or an excess of said vitamin D metabolite.

Any one or more metabolites of vitamin D may be measured in the method of the present invention. In a preferred embodiment, a specific vitamin D metabolite of interest is measured in a sample, although it is envisaged that for some applications it may be preferred to measure two or more types of the vitamin D metabolites in a sample. Preferably the vitamin D metabolite of interest is selected from the group consisting of 25-hydroxyvitamin $D_2$, 25-hydroxyvitamin $D_3$, 24,25-dihydroxyvitamin $D_3$, 25,26-dihydroxyvitamin D, and 1,25 dihydroxyvitamins $D_2$ and $D_3$. 25-hydroxyvitamins $D_2$ or $D_3$, are preferred vitamin D metabolites to be measured in the method of the invention. In a preferred embodiment the vitamin D metabolite is 25OH vitamin $D_3$.

By release of vitamin D is meant the full or partial separation of some or all of the vitamin D metabolites from vitamin D binding protein. It is preferred that substantially all of the vitamin D metabolites present in the sample are released from vitamin D binding protein.

It could now be shown and demonstrated that it is possible to release a vitamin D metabolite of interest out of its complex with vitamin D binding protein under conditions that allow for release of the vitamin D metabolite on the one hand and that do not cause protein precipitation on the other hand. In order to allow for release of the vitamin D metabolite an appropriate minimal concentration of a releasing reagent is required. The maximal concentration possible is the concentration still not causing precipitation of sample constituents, like proteins.

It has been found and established that efficacy of a vitamin D releasing reagent can be easily determined by use of the BIACORE system (GE Healthcare Bio-Sciences AB). For this assessment a streptavidin-coated BIACORE chip is used. This streptavidin-chip is then saturated with a biotinylated 25-hydroxyvitamin $D_3$ and thereafter with vitamin D binding protein. Thereafter vitamin D binding protein is released by applying the candidate vitamin D releasing reagent to the streptavidin/biotinyl-25-hydroxyvitamin $D_3$/vitamin D binding protein chip. The appropriate minimal concentration of a vitamin D releasing reagent is determined as the minimal concentration that results in the release of at least 99% of the bound vitamin D binding protein. These conditions mimic nicely the conditions found if vitamin D is released from its binding protein in a serum or plasma sample. The minimal concentration of a candidate vitamin D releasing reagent as determined in the BIACORE system is the same as the minimal concentration required for the efficient release of 25OH vitamin $D_3$ from vitamin D binding protein in a sample using that candidate vitamin D releasing reagent.

As mentioned the vitamin D binding protein in the BIACORE analysis is diluted in the candidate vitamin D releasing reagent. It is obvious to the skilled artisan that the minimal final concentration of the vitamin D releasing reagent in a mixture with the sample under investigation has to be at least the same concentration as the one determined by BIACORE analysis. If, e.g., sample and vitamin D releasing reagent are mixed 1:1, the releasing reagent has to be double concentrated as compared to the BIACORE setting before it is mixed with the sample. This way the minimal concentration determined as described above is present in the mixture of sample and releasing reagent.

Any vitamin D releasing reagent capable of achieving displacement, or separation, of the vitamin D metabolite 25-hydroxyvitamin $D_3$ from vitamin D binding protein and not resulting in protein precipitation may be used in step (a) of the method of the invention.

Preferred agents for use in the present invention are chemical reagents which may act by disrupting or destroying the bond between a vitamin D metabolite and vitamin D binding.

In a preferred embodiment the vitamin D releasing reagent is based on a salt with a cation having a quaternary nitrogen-based ion. Also preferred the releasing reagent is based on a salt having a quarternary N-heterocycle as a cation. Preferred cations are selected from the group consisting of pyrazolium cations, imidazolium cations, triazolium cations, pyridinium cations, pyridazinium cations, pyrimidinium cations, pyrazinium cations and triazinium cations. Preferred cations are those based on an imidazolium heterocyclic nucleus. Preferably the anion is selected from halogenated inorganic anions, nitrates, sulphates, carbonates, sulphonates and carboxylates. Preferably the anion may be selected from chloride, hexafluorophosphate, tetrafluoroborate, trifluoroacetate, benzoate, salicylate, and rhodanide. Combinations of the above cations and anions in most cases are extremely good miscible with water. Many are even soluble without water.

Appropriate reagents for release of vitamin D are preferably selected from the group consisting of 1-Butyl-4-methylpyridinium tetrafluoroborate; 1-Butyl-3-methyl-imidazolium tetrafluoroborate; 1-Butyl-3-methyl-imidazoliumoctylsulfate; 1-Butyl-3-methylpyridiniumchloride; 1-Hexylpyridiniumchloride; 1-Methyl-1-octyl pyrrolidiniumchloride; N-Octylpyridiniumchloride; 3-Carbamoyl-1-octyloxymethyl pyridiniumchloride; KBr; KJ; and KSCN, and of combinations thereof. Preferably such combination comprises five or less of these compounds. Preferably a mixture of four, three or two of these compounds can be used. Also preferred is the use of a single compound.

The reagent for differential hemolysis may also be selected from the group consisting of 1-Butyl-4-methylpyridinium tetrafluoroborate; 1-Butyl-3-methyl-imidazolium tetrafluoroborate; 1-Butyl-3-methyl-imidazoliumoctylsulfate; 1-Butyl-3-methylpyridiniumchloride; 1-Hexylpyridiniumchloride; 1-Methyl-1-octyl pyrrolidiniumchloride; N-Octylpyridiniumchloride; and 3-Carbamoyl-1-octyloxymethyl pyridiniumchloride. It is further preferred to use a mixture of at least one of these reagents and of KSCN.

As described above, a method for online chromatographic determination of a vitamin D metabolite out of a serum or plasma sample would be highly desirable. Surprisingly it could now be established that such method is feasible and has obvious advantages to the routine measurement of a vitamin D metabolite. In order to meet these requirements the vitamin D metabolite has to be efficiently released, but at the same time the appropriate vitamin D releasing reagent must not cause protein precipitation.

Protein precipitation in the sense of the present invention is assessed by applying in a standardized manner a sample of plasma or serum treated with a candidate vitamin D releasing reagent to a standard frit, e.g., to a frit as part of an HPLC column.

To assess whether a candidate vitamin D releasing reagent does not cause precipitation, i.e., is appropriate for latter online LC, said reagent is mixed 1 to 1 with a sample of plasma or serum and incubated for at least 15 min and for at most 60 min at 20° C. 50 aliquots of 10 μL of the thus processed sample are applied to a frit with a diameter of 2 mm and 0.5 μm pore size. The back-pressure is monitored. A candidate reagent for release of vitamin D that would cause an increase in back-pressure of 20 bar or more—if the back-pressure for injection 50 and the back-pressure for the first injection are compared to each other—would be deemed not to be appropriate. The maximal concentration of an appropriate vitamin D releasing reagent thus can easily be identified as not causing an increase in back-pressure at all or by causing an increase in back-pressure of less than 20 bar in the above analysis.

Preferably the filter used in the above analysis is an HPLC frit. Preferably such frit is made of stainless steel and is 1/32 inch thick. Also preferred the frit is part of an HPLC column of 20 mm in length, having an inner column diameter of 2 mm that is filled with 3.5 μm SYMMETRY C18 particles (Waters Corporation) with a pore size of 100 A° as bed material.

As the skilled artisan will readily appreciate the serum or plasma sample used for such assessment is obtained from a healthy individual, i.e., an individual having no known disease and biochemical values in the normal range.

Preferably the appropriate vitamin D releasing reagent is further characterized in that the (minimal) concentration required for release of vitamin D from vitamin D binding protein and the (maximal) concentration tolerated and not causing precipitation are at least two-fold apart. The broader the window between minimal and maximal concentration the more easy such reagent can be used in clinical diagnostic routine. It is further preferred that the vitamin D releasing reagent is used at a final concentration corresponding to the mean value plus/minus 25% of the minimal concentration and the maximal concentration. Further preferred the final concentration will be adjusted to be within plus or minus 20% of the mean value of minimal and maximal concentration.

Whereas the prior art reagents like ethanol or acetonitrile all cause precipitation if used in a high concentration several of the now investigated reagents can be used in very high concentrations without causing protein precipitation at all. Preferably the vitamin D releasing reagent of the present invention is used at a concentration of no more than 75% weight/volume, also preferred at no more than 50% weight/volume.

A plasma or serum sample treated with an appropriate vitamin D releasing reagent according to the present invention can be directly subjected to liquid chromatography.

Liquid chromatography (LC) is an extremely important analytical technique which is used for the separation, identification and quantitation of an analyte of interest, e.g. of a vitamin D metabolite, During LC the chemical components in a mixture are carried through a stationary phase by the flow of a liquid mobile phase. Separation in liquid chromatography is achieved by means of differences in the interactions of the analytes with both the mobile and stationary phases. As the skilled artisan appreciates both a stationary phase and a mobile phase appropriate to the analytes under investigation have to be chosen. In addition, the user will identify chromatographic conditions appropriate to maintain the sharpness of analyte bands or peaks as a sample moves through the stationary phase column to the detector.

High Performance Liquid Chromatography, also known as High Pressure Liquid Chromatography, abbreviated as HPLC, is a special form of liquid chromatography and nowadays used frequently in biochemistry and analytical chemistry. The analyte is forced through a column of the stationary phase in a liquid (mobile phase) at high pressure, which decreases the time the separated components remain on the stationary phase and thus the time they have to diffuse within the column. This leads to narrower peaks in the resulting chromatogram and thence to better resolution and sensitivity as compared to LC.

The mobile phase is chosen to ensure solubility of the sample solutes. For the stationary phase, preferably micro particulate silica (bare or chemically modified) is used, because its high surface area accentuates the differences in solute-stationary phase interactions. The use of a stationary phase that interacts strongly with solutes relative to solute mobile-phase interactions will result in very long retention times, a situation which is not analytically useful. Hence the stationary phase must be selected so as to provide weak to moderate solute interactions relative to those in the mobile phase. As a consequence, the nature of the solute governs the type of LC selected. The stronger interactions should occur in the mobile phase to ensure sample solubility and ready elution, while the stationary phase should be responsive to more subtle differences among the solutes. For example, polar neutral compounds are usually better analyzed using a polar mobile phase together with a nonpolar stationary phase that distinguishes subtle differences in the dispersive character of the solutes. One of the powerful aspects of HPLC is that the mobile phase can be varied to alter the retention mechanism. Modifiers can be added to the mobile phase to control retention. For example, pH is an important variable in aqueous mobile phases.

Five general classes of LC can be distinguished:

1. Normal-phase chromatography calls for the use of a polar stationary phase in conjunction with a non-polar (dispersive) mobile phase.

2. Reversed-phase chromatography, the opposite possibility, calls for the use of a non-polar stationary phase and a polar mobile phase (composed of one or more of the polar solvents, e.g., water, methanol, acetonitrile, and tetrahydrofuran).

3. Ion-exchange chromatography involves ionic interactions. In this ease the mobile phase must support ionization to ensure solubility of ionic solutes. The stationary phase must also be partially ionic to promote some retention. Consequently, the interactions with the stationary phase are strong, and this is usually reflected in longer analysis times and broad peaks.

4. Size-Exclusion chromatography involves separations based on molecular size alone and ideally requires that there be no energetic interaction of the solutes with the stationary phase.

5. Affinity chromatography is based on a specific interaction, e.g., between the members of a specific binding pair, like antigen and corresponding antibody or receptor and corresponding ligand. For example a first partner of a binding pair is bound to an appropriate stationary phase and used to capture the second partner of the binding pair. The second partner can be released and isolated by appropriate means.

The general classification of separation principles given above must not be exhaustive and therefore is non-limiting, there are other separation principles which can be used for the separation of liquid samples, e.g., hydrophobic interaction chromatography, hydrophilic interaction chromatography, ion-pair chromatography, molecular imprinted materials based separation.

In routine applications the stationary phase, the so-called bed material, e.g., silica particles in an RP-HPLC-application, is packed into an appropriate column, and is protected by a fit. The frit material usually is selected to have, e.g., a smaller pore size as compared to the interparticle pore size of the bed material.

In HPLC methods the diameter of the stationary phase particles usually is in the range of 1 to 10 μm. These small particles necessitate the high pressure used in HPLC. The bed material usually is protected by a frit. Typical frits have a pore size of 1 μm, 0.45 μm or 0.2 μm. The smaller the particles the smaller is usually the pore size of the frit. If a sample comprises a constituent capable of blocking an HPLC fit this is detrimental for any routine analysis. As the skilled artisan will appreciate blocking of the frit used in an HPLC column will occur the more rapidly the smaller the pore size of the frit and the smaller the column and correspondingly the fit diameter. In case the frit would not be selected appropriately, a too large pore size, the particle size of the column material would also matter and the column itself would block more rapidly the smaller the particles are. However, the skilled artisan will select the pore size of the frit to meet the requirements for protecting the column bed material.

If a plasma or serum sample, is, e.g., treated with acetonitrile to release vitamin D from its complex with vitamin D binding protein a lot of proteins are denatured and precipitate. Such sample can not be applied to an HPLC column in any routine setting, because it would block the column and cause a system shut down.

By treating a serum or a plasma sample with a vitamin D releasing reagent according to the present invention it is now possible to directly apply such treated sample to an HPLC column, without running the risk of blocking the column. Preferably this HPLC step is perforated online with the sample obtained by treatment with the vitamin D releasing reagent. Preferably, the stationary phase particles used in such HPLC step are in the range of 1 to 10 μm, also preferred in the range of 2 to 7 μm in diameter. Preferably the frit used in such HPLC step has a pore size of 0.5 μm or also preferred of 0.2 μm.

As mentioned above, care has to be taken that the vitamin D releasing reagent does not cause protein precipitation.

The analyte of interest can be detected by any appropriate means. Appropriate and preferred detectors sense the presence of a compound passing through, and provide an electronic signal to a recorder or computer data station. The output is usually in the form of a chromatogram and a substance of interest is usually found in a certain peak. The peak area or the height of the peak can be used to quantify the amount of analyte present in the sample investigated.

The detector for an HPLC system is the component that emits a response due to the eluting sample compound and subsequently signals a peak on the chromatogram. It is positioned immediately posterior to the stationary phase in order to detect the compounds as they elute from the column. The detection and sensitivity parameters may be controlled by the skilled artisan. There are many types of detectors that can be used with HPLC. Some of the more common detectors include: Refractive Index (RI), Ultra-Violet (UV), Fluorescent, Radiochemical, Electrochemical, Near-Infra Red (Near-IR), Mass Spectroscopy (MS), Nuclear Magnetic Resonance (NMR), and Light Scattering (LS).

Refractive Index (RI) detectors measure the ability of sample molecules to bend or refract light. This property for each molecule or compound is called its refractive index. For most RI detectors, light proceeds through a bi-modular flow-cell to a photodetector. One channel of the flow-cell directs the mobile phase passing through the column while the other directs only the mobile phase. Detection occurs when the light is bent due to samples eluting from the column, and this is read as a disparity between the two channels.

Fluorescent detectors measure the ability of a compound to absorb and then re-emit light at given wavelengths, respectively. Each compound able to emit the fluorescence light has a characteristic excitation and emission wavelength. The excitation light passes through the flow-cell while the photodetector in orthogonal position measures the emitted light at specific wavelength.

Radiochemical detection involves the use of radiolabeled material, usually tritium (3H) or carbon-14 (14C). It operates by detection of fluorescence associated with beta-particle ionization, and it is most popular in metabolite research.

Electrochemical detectors measure compounds that undergo oxidation or reduction reactions. This is usually accomplished by measuring gain or loss of electrons from migrating samples as they pass between electrodes at a given difference in electrical potential.

Mass spectrometry is an analytical technique used to measure the mass-to-charge ratio (m/z (or m/q)) of ions. It is most generally used to analyze the composition of a physical sample by generating a mass spectrum representing the masses of sample components. The technique has several applications, including: identifying unknown compounds by the mass of the compound and/or fragments thereof; determining the isotopic composition of one or more elements in a compound; determining the structure of compounds by observing the fragmentation of the compound; quantitating the amount of a compound in a sample using carefully designed methods (mass spectrometry is not inherently quantitative); studying the fundamentals of gas phase ion chemistry (the chemistry of ions and neutrals in vacuum); determining other physical, chemical or even biological properties of compounds with a variety of other approaches.

A mass spectrometer is a device used for mass spectrometry, and produces a mass spectrum of a sample to analyze its composition. This is normally achieved by ionizing the sample and separating ions of differing masses and recording their relative abundance by measuring intensities of ion flux. A typical mass spectrometer comprises three parts: an ion source, a mass analyzer, and a detector.

The kind of ion source is a contributing factor that strongly influences what types of samples can be analyzed by mass spectrometry. Electron ionization and chemical ionization are used for gases and vapors. In chemical ionization sources, the analyte is ionized by chemical ion-molecule reactions during collisions in the source. Two techniques often used with liquid and solid biological samples include electrospray ionization (ESI) and matrix-assisted laser desorption/ionization (MALDI). Other techniques include fast atom bombardment (FAB), thermospray, atmospheric pressure chemical ionization (APCI), secondary ion mass spectrometry (SIMS) and thermal ionisation.

Nuclear magnetic resonance (NMR) detection is based on the fact that certain nuclei with odd-numbered masses, including H and $^{13}C$, spin about an axis in a random fashion. However, when placed in a strong magnetic field, the spins are aligned either parallel or anti-parallel to the magnetic field, with the parallel orientation favored since it is slightly lower in energy. That magnetic nuclei can absorb RF energy when placed in a magnetic field of a specific strength. When this absorption occurs, the nucleus is said to be on resonance. Interestingly for analytical scientists, different atoms within a molecule resonate at different frequencies at a given field strength. The observation of the resonance frequencies of a molecule allows a user to discover structural information about the molecule.

When a source emits a parallel beam of light which strikes particles in solution, some light is reflected, absorbed, transmitted, or scattered. These phenomena can be measured by a light-scattering (LS) detector. The most prominent forms of LS detection are termed nephelometry and turbidometry. Nephelometry is defined as the measurement of intensity of scattered light emanated from an illuminated volume of a suspension. The ratio of scattered intensity to illuminating intensity is compared with a standard of known properties. Turbidometry is defined as the measure of the reduction of light transmitted due to particles in solution. It measures the light scatter as a decrease in the light that is transmitted through the particulate solution. Therefore, it quantifies the residual light transmitted.

Near-infrared detectors operate by scanning compounds in a spectrum from 700 to 1100 nm. Stretching and bending vibrations of particular chemical bonds in each molecule are detected at certain wavelengths.

A vitamin D metabolite is preferably detected by mass spectroscopy.

In a further aspect the method according to the present invention is used for determining the vitamin D status of a subject.

In a further embodiment of the invention, there is provided a kit comprising a vitamin D releasing reagent according to the present invention. The kit preferably also comprises a key showing the correlation between the results of the assay with the amount of vitamin D metabolite present in the sample. The kit preferably will also comprise instructions for use.

A big advantage of the method according to the present invention is that in case a diagnostic need exists to assess more than one vitamin D metabolite, this can easily be accomplished. Preferably the sample is analyzed for at least two vitamin D metabolites of interest that are selected from the group consisting of 25-hydroxyvitamin $D_2$, 1,25-dihydroxyvitamin $D_3$, 25-hydroxyvitamin $D_3$, 24,25-dihydroxyvitamin $D_3$, 25,26-dihydroxyvitamin $D_3$.

Preferably 25 OH vitamin $D_3$, 1,25-dihydroxyvitamin $D_3$ and 24,25 dihydroxyvitamin $D_3$ are assessed in one run using the method according to the present invention. The method according to the present invention can be combined with the advantages of using an isotope-labeled internal standard.

In a preferred embodiment the present invention relates to a method of measuring a vitamin D metabolite in a sample, the method comprising the steps of
 (a) adding an isotope labeled vitamin D metabolite to said sample,
 (b) treating said sample with a releasing reagent under conditions appropriate to release the vitamin D metabolite from vitamin D-binding protein,
 (c) subjecting the treated sample obtained in step (b) to liquid chromatography, and
 (d) measuring the vitamin D metabolite during or after liquid chromatography, preferably by mass spectroscopy.

In a further preferred embodiment the present invention relates to a vitamin D releasing reagent appropriate to release 25 OH-vitamin D from vitamin D binding protein and not to cause protein precipitation, which additionally comprises an isotope-labeled vitamin D metabolite. Said isotope-labeled vitamin D metabolite preferably is an isotope-labeled 25 OH-vitamin $D_3$. The concentration of the isotope-labeled vitamin D metabolite is known and preferably adjusted to match the physiologically relevant concentration of the vitamin D metabolite of interest.

In yet a further embodiment the present invention relates to a kit comprising a vitamin D releasing reagent and in addition an isotope-labeled vitamin D metabolite, wherein said isotope-labeled vitamin D metabolite may be present as a separate component or is already contained within the vitamin D releasing reagent and wherein said releasing reagent is based on a salt having a quaternary N-heterocycle as a cation.

The following examples and figures are provided to aid the understanding of the present invention, the true scope of which is set forth in the appended claims. It is understood that modifications can be made in the procedures set forth without departing from the spirit of the invention.

Example 1

Synthesis of a biotinylated 25-hydroxyvitamin $D_3$-conjugate

The steps used in the synthesis of the biotin-25-hydroxyvitamin $D_3$-conjugate are depicted schematically in FIG. 1.

In this synthesis 25-hydroxyvitamin $D_3$ is chemically activated at position 3 of the vitamin D scheme depicted in Formula I. In 25-hydroxyvitamin $D_3$ position 25 of Formula I is carrying an OH-group, Formula I

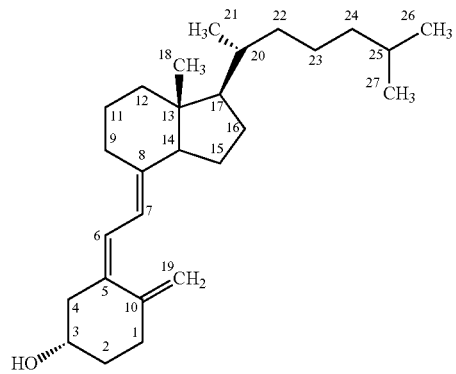

1.1 Synthesis of a 25-hydroxyvitamin $D_3$-3-2'-cyanoethylether

In a round-bottomed flask with three necks and equipped with an internal thermometer 20 mg (50 µmol) 25-hydroxyvitamin $D_3$ (Sigma-Aldrich, no. H-4014) are dissolved in 10 ml dry acetonitrile under argon atmosphere. The solution is admixed with 1.5 ml tert.-butanol/acetonitrile (9:1) and then cooled down to 6° C. in an ice bath. Then 820 µl of an acrylnitrile solution (from a solution of 86 µl acrylnitrile in 1.0 ml acetonnitrile) are added and the mixture is stirred and incubated for 15 min at 6° C. Thereafter 205 µl of an organic potassiumhydrid-solution (25 mg KH in 0.5 ml tert.-butanol/acetonitrile 9:1) are added. The reaction mixture is incubated under stirring for 45 min at 6° C. and thereafter for an additional 60 min at 4° C. For a short time an intermediate precipitate is formed and thereafter a clear solution is obtained. Thereafter the reaction mixture is diluted with 10 ml methyl-tert.-butylether and then washed twice with 10 ml $H_2O$. The organic phase is dried by adding 1 g water free sodium sulfate, filtered through a G3 frit and finally the organic solvent is removed by applying a vacuum. The remaining viscous solid is further dried by applying high-vacuum. About 55 mg color free dry viscous material is obtained in this step.

1.2 25-hydroxyvitamin D-3-3'-aminopropylether

The nitrile obtained in step 1.1 is dissolved in 15 ml diethylether. Under stirring a suspension consisting of 7.5 mg lithiumhydrid in 7.5 ml diethylether is added. The mixture is stirred for one hour at room temperature (RT). Thereafter a suspension of 38.4 mg lithiumaluminumhydrid in 6.6 ml diethylether is added. The reaction mixture turns turbid and is stirred for a further hour at RT. Thereafter the reaction mixture is cooled to 0-5° C. in an ice bath and slowly diluted by adding 35 ml of water in total. By adding 6.6 ml of a 10 M KOH the pH-value turns highly alkaline.

The organic material is extracted thrice with 65 ml methyl-tert.-butylether, each. The pooled organic phase is dried by adding 5 g of water free sodium sulfate, filtered through a G3 frit and finally the organic solvent is removed by applying a vacuum. The remaining viscous solid is further dried by applying high-vacuum. The raw material obtained in this step is dissolved in a mixture of 5 ml DMSO and 3.0 mL acetonitrile and purified via preparative HPLC. The eluents used are: Eluent A=$H_2O$ with 0.1% trifluoro acetic acid (TFA); and eluent B=95% acetonitrile+5% $H_2O$ with 0.1% TFA. The gradient applied goes within 100 min from 50% eluent B to 100% eluent B. The column material is Vydac C18/300 Å/15-20 µm and the column has a diameter of 5 cm and a length of 25 cm. Chromatography is performed at RT with a flow rate of 30 ml/min. The elution is monitored at 226 nm. The fractions comprising the desired product in a purity of at least 85% as determined by analytical HPLC (Vydac C18/300 Å/5 µm/; 4.6×250 mm) are pooled and lyophilized. The yield of the desired color free product is about 70%.

1.3 Synthesis of the 25-hydroxyvitamin $D_3$-3-3'-N-(hemisuberyl)amino-propylether-biotin-(beta-Ala)-Glu-Glu-Lys(epsilon)-conjugate 15.9 mg (35 µmol) 25-hydroxyvitamin $D_3$-3-3-'-amino-propylether (obtained as described in step 1.2) are dissolved in 3.5 ml DMSO. 34.4 mg (42 µmol) biotin-(beta-Ala)-Glu-Glu-Lys(epsilon)-hemisuberat-N-hydroxysuccinimideester (Roche Applied Science, Nr. 11866656) and 15 µl triethylamine are added and the mixture is stirred over night at RT. The reaction mixture is diluted with 4.5 ml DMSO filtered over a 0.45 µm microfilter and finally subjected to preparative HPLC. In this preparative HPLC the conditions as described in example 1.2 are applied. The fractions comprising the desired product in a purity of at least 85% as determined by analytical HPLC (Vydac C18/300 Å/5 µm/; 4.6×250 mm) are pooled and lyophilized. The yield of the desired 25-hydroxyvitamin $D_3$-3-3'-N-(hemisuberyl)aminopropylether-biotin-(beta-Ala)-Glu-Glu-Lys(epsilon)-conjugate or simply, "25-hydroxyvitamin $D_3$-biotin" is about 36%.

Example 2

Assessment of Release of Vitamin D from Vitamin D Binding Protein

The BIACORE system is used to assess whether a reagent considered to be a potential candidate for releasing vitamin D from vitamin D binding protein will be efficient in releasing of vitamin D binding protein to a vitamin D metabolite.

A sensor chip coated with streptavidin (Sensor Chip SA, BIACORE AB, BR-1000-32) is used for immobilization of a biotinylated vitamin D metabolite of interest. The assessment is best performed by use of the vitamin D metabolite 25OH vitamin $D_3$.

The sensor chip is first incubated with a saturating concentration of biotinylated 25-hydroxyvitamin $D_3$, Then the chip is loaded with a saturating amount of vitamin D binding protein. Then the vitamin D binding protein saturated chip is incubated with a sodium chloride solution one the one hand and a candidate vitamin D releasing reagent in various concentrations on the other hand. The release of vitamin D binding protein is monitored for 3 min. A candidate vitamin D releasing reagent causing the release of at least 99% vitamin D binding protein in the above system is appropriate to meet the minimal requirements for a vitamin D releasing reagent used in the detection of a vitamin D metabolite in a sample of serum or plasma 25-hydroxyvitamin $D_3$.

Between each run the 25-hydroxyvitamin $D_3$-coated SA-chip is regenerated by washing it with 10 mM Gly/HCl pH 1.7 for 1 min. As non-specific control a reference flow cell coated with biotin on the same chip was used. The data of the reference flow cell are subtracted from those of the biospecific flow cell. Thus specific data free of non-specific effects are obtained.

TABLE 1

Concentration of releasing reagent required for release off >95% vitamin D binding protein from 25OH-vitamin $D_3$

| releasing reagent | | % volume/ volume |
|---|---|---|
| BMP-TFB | 1-Butyl-4-methyl-pyridinium-tetrafluoroborate | 6 |
| BMI-TFB | 1-Butyl-3-methyl-imidazolium-tetrafluoroborate | 8 |
| BMI-OSO4 | 1-Butyl-3-methyl-imidazolium-octylsulfate | 0.5 |
| BMP-Cl | 1-Butyl-3-methyl-pyridinium-chloride | 12 |
| BMP-SCN | 1-Butyl-3-methyl-pyridinium-thiocyanate | 6 |
| HP-Cl | 1-Hexylpyridinium-chloride | 6 |
| MOP-Cl | 1-Methyl-1-octyl-pyrrolidinium-chloride | 3 |
| NOP-Cl | N-Octylpyridinium-chloride | 3 |

Figure 2:
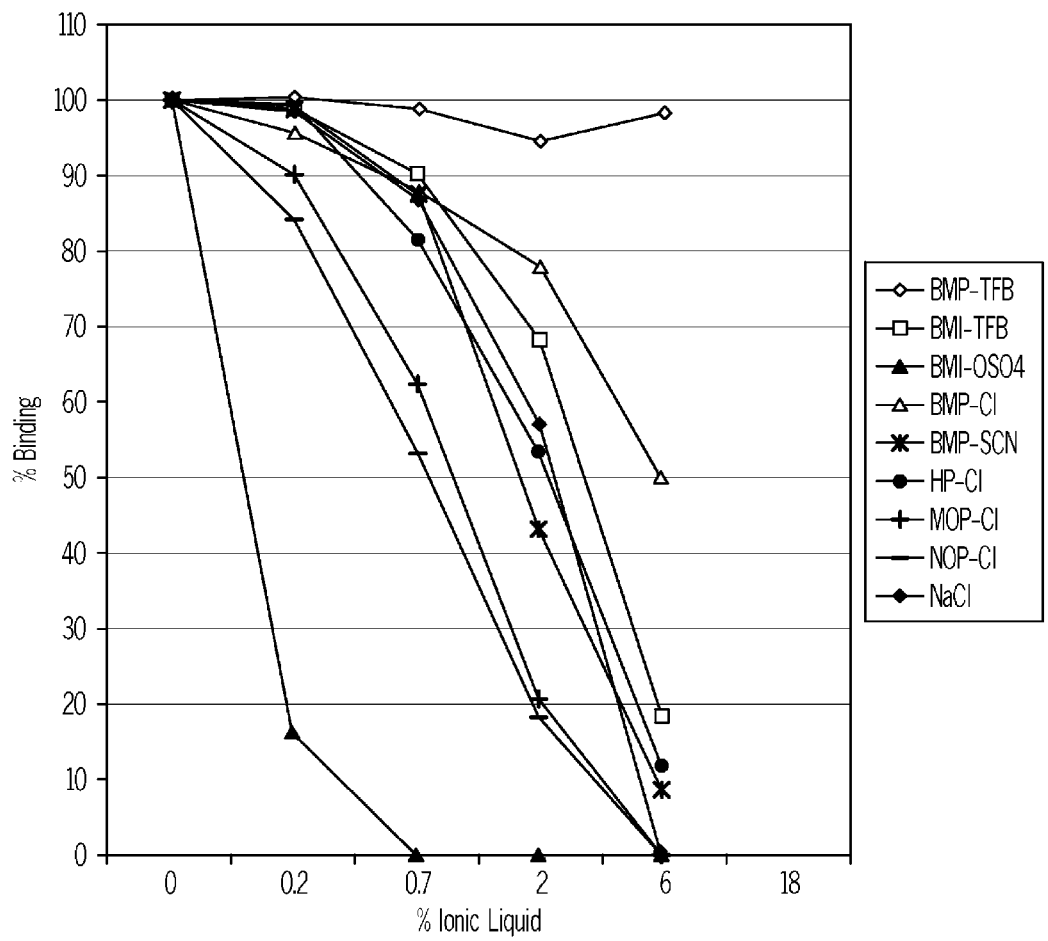
FIG. 2: Separation of vitamin D binding protein from 25-hydroxyvitamin $D_3$ For each of the releasing reagents tested the concentration dependency is shown.

As can be seen from the above Table 1, efficient separation of 25OH-vitamin $D_3$ and vitamin D binding protein is possible with any of the reagents given there. The concentration dependency of this separation is further illustrated in FIG. 2.

Example 3

Method for the Quantification of Circulating 25-Hydroxyvitamin $D_3$ Using Liquid Chromatography-Tandem Mass Spectrometry A straightforward isotope dilution liquid chromatography-tandem mass spectrometry method for detection of 25-hydroxyvitamin $D_3$ has been developed. The method is similar to Vogeser et al. supra, in brief this method works as follows:

Stable isotope-labeled 25-hydroxyvitamin $D_3$ is used for internal standardization. Acetonitrile is added to the sample in order to release the analyte from vitamin D binding protein. Manual protein precipitation is performed, followed by online automated solid phase extraction with direct transfer to the tandem mass spectrometry system. Atmospheric pressure chemical ionization (APCI) in the positive mode is used. For native 25-hydroxyvitamin $D_3$, the transition 401>257 m/z is recorded. For the internal standard labeled with six deuterium atoms, the transition 407>263 is recorded.

Analytical Procedure:
Standards 25-hydroxyvitamin $D_3$ (25-hydroxycholecalciferol) is procured from Sigma (Deisenhofen, Germany) (purity 98%; molecular weight 400.7). A stock solution with a concentration of 3250 nmol/L is prepared in methanol.

For use as an internal standard, stable isotope-labeled 25-hydroxyvitamin $D_3$ is bought from Synthetica (Sweden) 26,27-hexadeuterium-25-hydroxyvitamin D3 (chemical purity 95%, isotopic purity 99.9%). A working internal standard solution with a concentration of 570 nmol/L is prepared in methanol.

An Agilent HPLC 1100 with binary gradient system, degasser and Autosampler is used. The mass spectrometer used is a triple quadrupol Quantum Ultra EMR from Thermo Electron with APCI ion source.

100 µl of serum are pipetted into 2 ml polypropylene cups, then 25 µL of the internal standard working solution is added. After vortex mixing, the samples are placed on a vortexer for 5 minutes at room temperature. For equilibration, the samples are then kept at 37° C. for two hours. 300 µL acetonitrile are added to release the analyte and the stable isotope-labeled internal standard from the protein bonds and to precipitate proteins. The samples are placed on a vortex mixer for 10 min and then kept at 4-8° C. for one hour. After centrifugation for 20 minutes at 16,000 g in a standard bench top centrifuge, a clear supernatant and a stable protein pellet are obtained. The supernatant is transferred to a HPLC vial and placed in the auto sampler.

For online solid phase extraction, LiChrospher RP-18 ADS, 25 µm, 25×4 mm extraction column (Merck) is used in combination with a Rheodyne six-port high-pressure switching valve The automated solid phase extraction procedure consisted of five steps:
1. Injection of the deproteinized sample onto the ADS extraction column (FIG. 3) with eluent A (5% methanol in water, flow rate 3 mL/min). Hydrophilic sample components are removed and transferred to the waste. Simultaneously the analytical column is equilibrated with eluent C (90% methanol, 10% 0.5 mM ammonium acetate, flow rate with a step flow gradient: 0-9 min 0.85 mL/min and 9-17 min 1.2 mL/min)
2. The enriched analyte from the extraction column is transferred to the analytical column in the back flush mode with eluent C. (FIG. 4)
3. Isocratic elution of the analyte from the analytical column and separation of matrix components with eluent C and the extraction column is regenerated with eluent B (methanol/acetonitrile 50/50, flow 3 mL/min) (FIG. 5)
4. Equilibration of the system with increased flow rate eluent C (FIG. 3)
5. Transfer of late eluting matrix components to the waste (FIG. 6)

Figure 3:
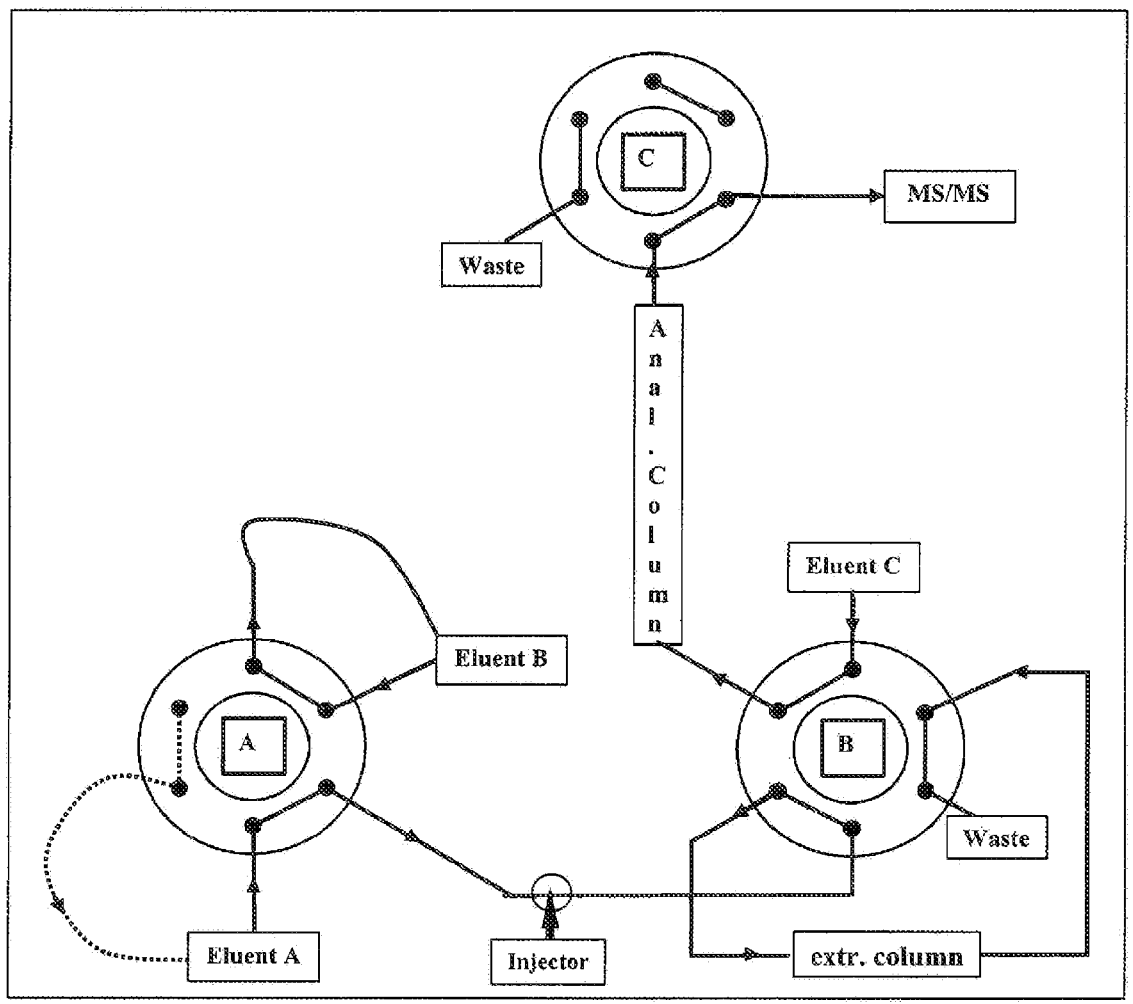
FIG. 3: Sample injection. The valve settings of the automated HPLC system for sample injection mode and wash mode are given.
Figure 4:
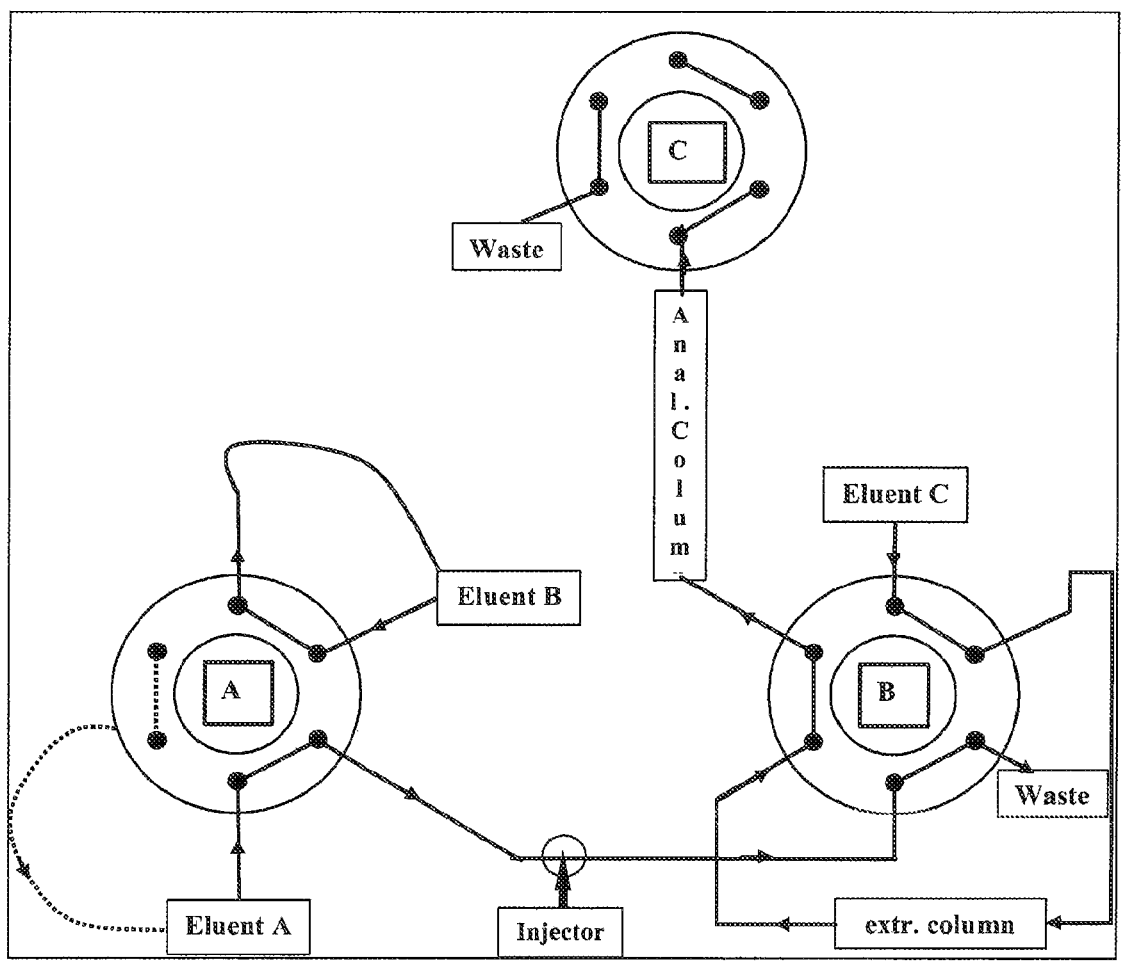
FIG. 4: Analyte transfer. The valve settings of the automated HPLC system for transfer of the analyte containing fraction from the extraction column to the analytical column are shown.
Figure 5:
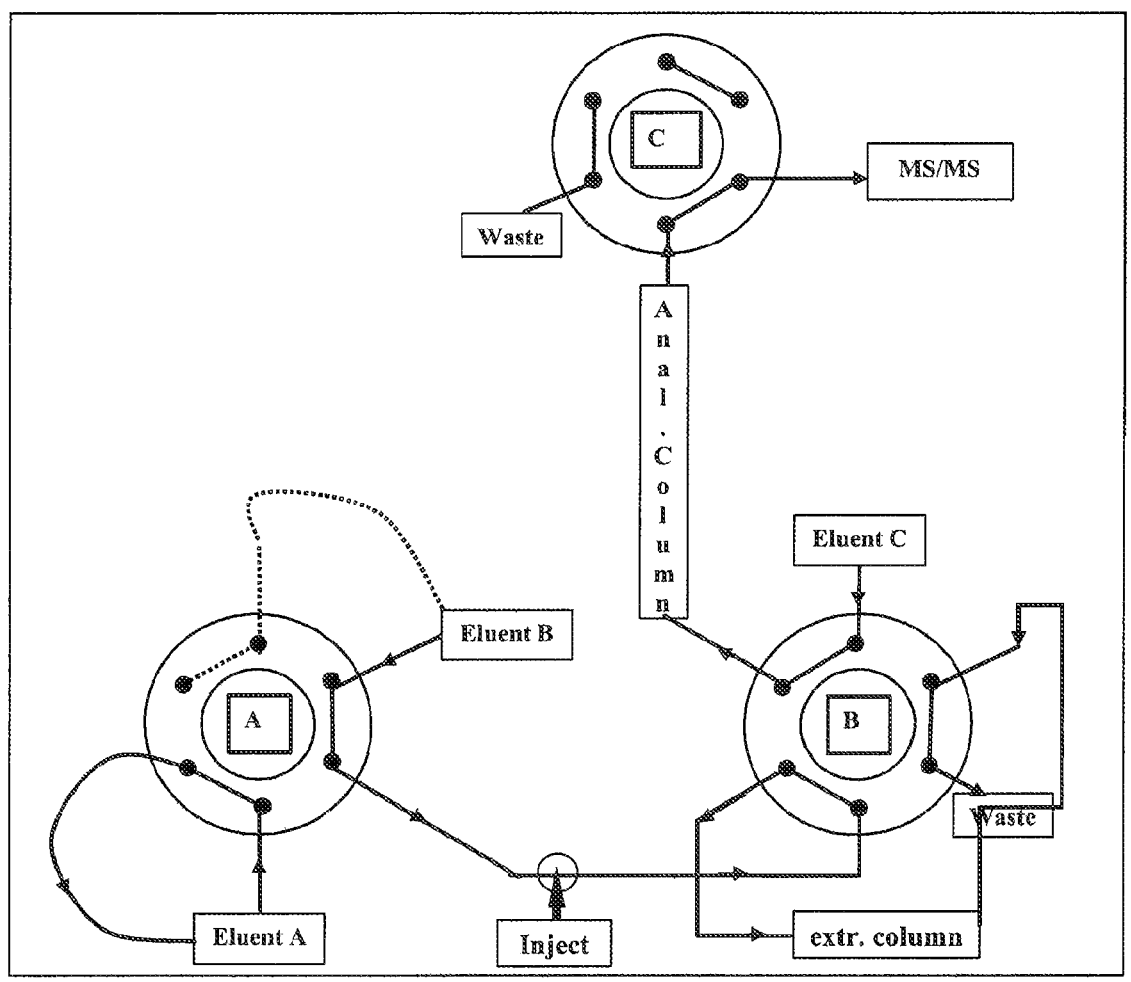
FIG. 5: Analyte elution. The valve settings of the automated HPLC system for isocratic analyte elution from the analytic column are given.
Figure 6:
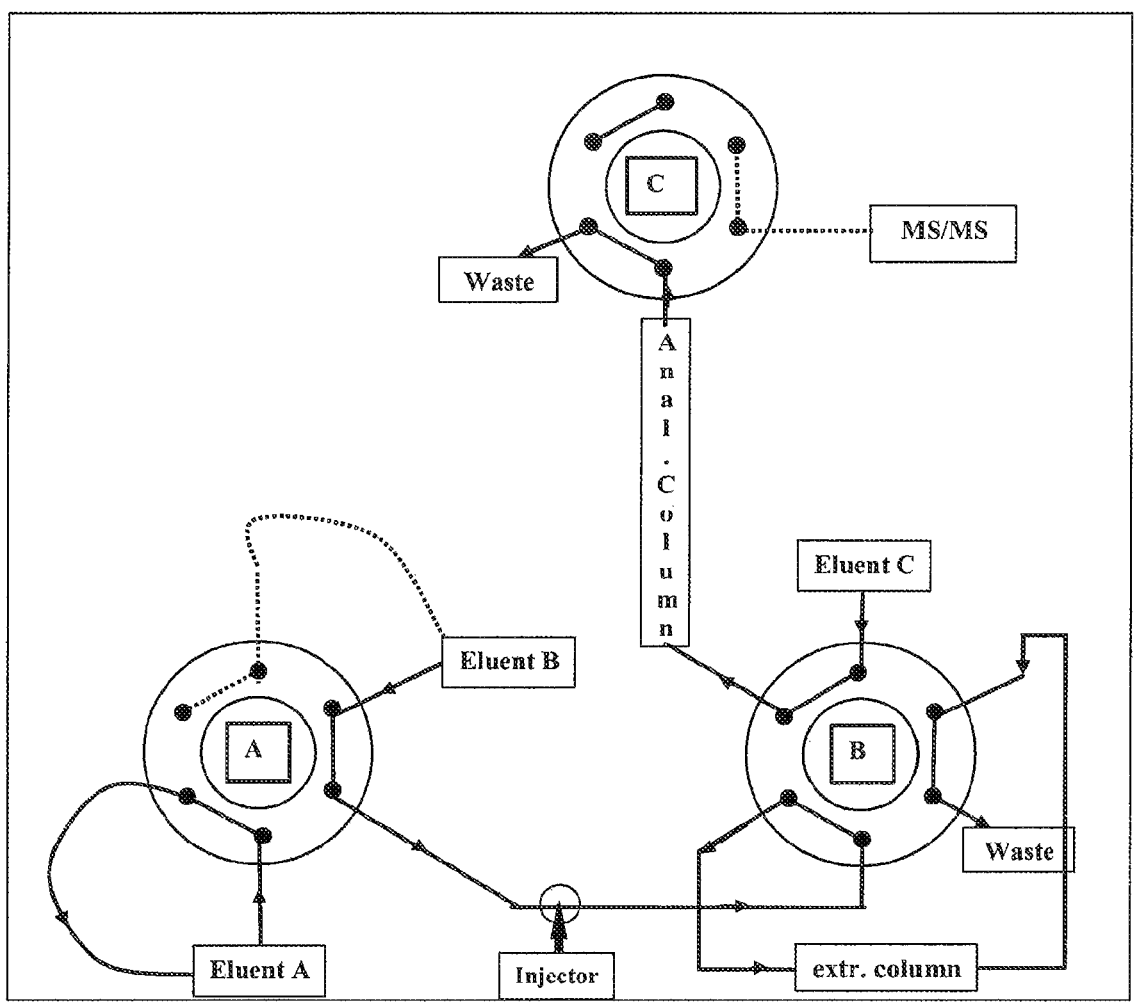
FIG. 6: Waste step. The valve settings of the automated HPLC system for transfer of the late eluting sample components to the waste are shown.
Figure 7:
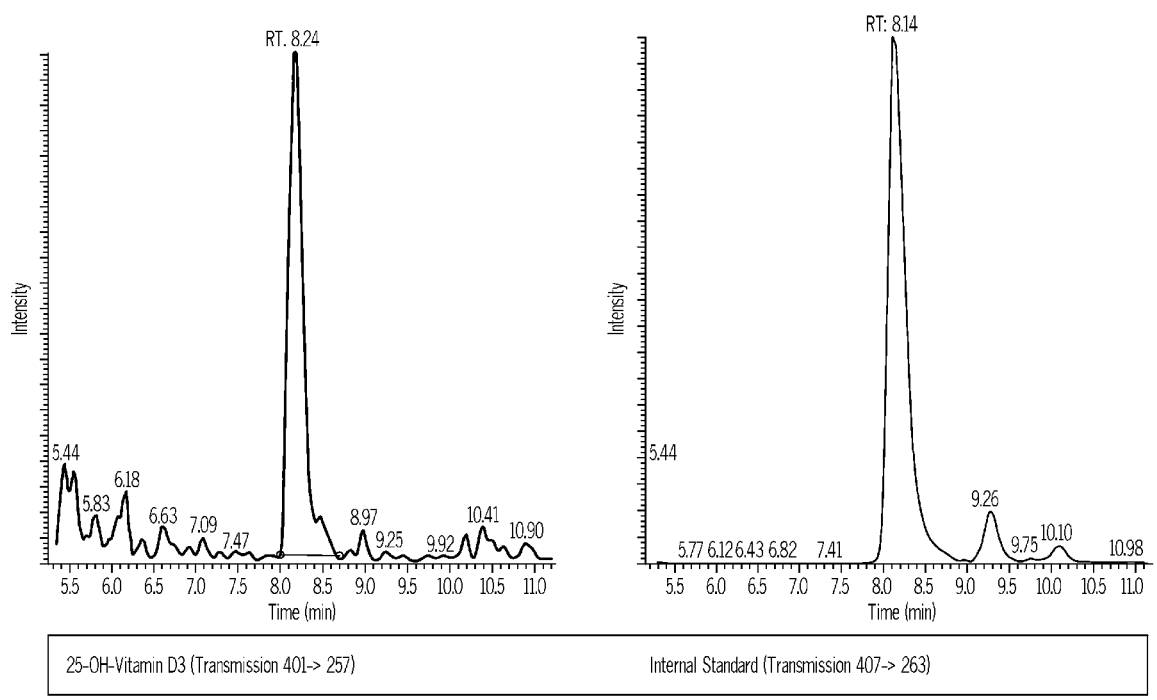
FIG. 7: Typical chromatogram. On the left hand side a typical chromatogram for the m/z transition from 401 to 257 of is given. On the right hand side a typical chromatogram for the m/z transition from 407 to 263 of isotope-labeled 25-hydroxyvitamin $D_3$ is given.

A typical chromatogram is shown in FIG. 7.
Time Table for Column Switching:

| Time [min] | Valve A | Valve B | Valve C | Description |
|---|---|---|---|---|
| 0 | 1 | 1 | 1 | FIG. 3 |
| 3 | 1 | 2 | 1 | FIG. 4 |
| 4 | 2 | 1 | 1 | FIG. 5 |
| 10 | 2 | 1 | 2 | FIG. 6 |
| 11 | 1 | 1 | 2 | equilibration and cleanup |
| 17 | Stop | | | |

Column temperatures: RT (trapping column)
30° C. (analytical column)
Injector temperature 8° C.
Injection volume: 70 µl Setting of MS/MS Parameters:

The parameters of the atmospheric pressure ion source (APCI) and the mass spectrometer tuning parameters are set and optimized according manufacturer instructions in order to obtain maximum sensitivity for HVD detection. MS analyser resolution is set to a peak width of 0.7 amu. Argon is used as collision gas, gas pressure is set to 1.5 mTorr, collision energy for MS/MS fragmentation is optimized to get maximum signal for ion transitions 401 to 257 (for 25OH-D3) and 407 to 263 (for the internal standard).

Figure 8:
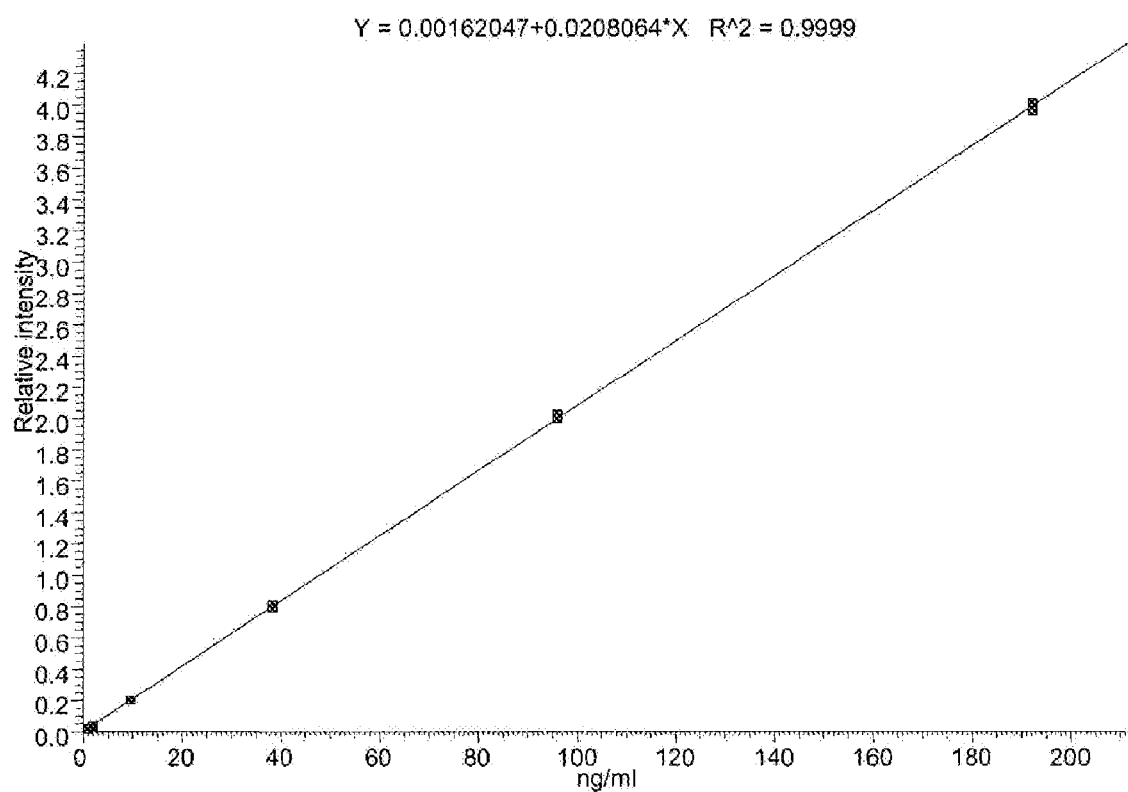
FIG. 8: Calibration curve. A typical calibration curve based on pure 25-hydroxyvitamin $D_3$ is depicted.

Calibration:

In the analytical series, a six-point calibration is performed using a pure solution of 25-hydroxyvitamin $D_3$ in methanol/water (1/1) covering the concentration range from 10 ng/mL up to 300 ng/mL. A typical calibration curve is given in FIG. 8.

Example 4

Method for the Quantification of Circulating 25-Hydroxyvitamin $D_3$ Including Release of Vitamin D from Vitamin D Binding Protein without Protein Precipitation Details of the procedure are as in example 3 but with a significant change in sample preparation.

100 µl of serum are pipetted into 2 ml polypropylene cups, then 25 µL of the internal standard working solution is added. After vortex mixing, the samples are placed on a vortexer for 5 minutes at room temperature. For equilibration, the samples are then kept at 37° C. for two hours.

To this equilibrated serum sample an aliquot of 100 µL Vitamin D releasing reagent is added. The vitamin D releasing reagent in this example consists of a 50% (weight/volume) solution of 1-Butyl-4-methylpyridinium tetrafluoroborate in water. The mixture is incubated for 20 minutes at room temperature and transferred to autosample of the HPLC system. The following procedure for detection of 25-hydroxyvitamin $D_3$ is identical to the one given in example 3.

Example 5

Results of Method Comparison

Four patient serum samples are processed according to the procedures from example 3 and example 4, respectively. The measurement according to the novel procedure (cf. example 4) has been repeated once and mean values are also given in table 2.

TABLE 2

Values for 25-hydroxyvitamin D3 obtained with two different methods

| | | LC-MS/MS according to example 3 | LC-MS/MS using a novel vitamin D releasing reagent | | |
|---|---|---|---|---|---|
| Serum Nr.: | Seren Code | ng/ml | 1. Inj. | 2. Inj. | mean |
| 40 | 9461-25819 | 10.0 | 12.4 | 12.2 | 12.3 |
| 41 | 9473-68813 | 14.9 | 14.1 | — | 14.1 |
| 44 | 9030-20136 | 35.4 | 39.5 | 31.3 | 35.4 |
| 46 | 3610-29487 | 25.9 | 25.8 | 29.3 | 27.6 |

As can be seen from Table 2 data gathered with the novel method are comparable to the data as gathered with the proposed reference method. The novel method has the advantage that the data are obtained without precipitation or centrifugation in an online HPLC MS/MS system.

What is claimed is:
1. A method of measuring a vitamin D metabolite in a sample, the method comprising the steps of:
  (a) treating said sample with a releasing reagent under conditions appropriate to release the vitamin D metabolite from a vitamin D-binding protein without causing precipitation of the protein,
  (b) subjecting the treated sample to liquid chromatography, and
  (c) measuring the vitamin D metabolite during or after liquid chromatography,
  wherein said releasing reagent comprises a salt having a quaternary N-heterocycle cation.

2. The method of claim 1, wherein said liquid chromatography is a column chromatography performed by use of a column comprising a frit and a bed material.

3. The method of claim 2, wherein said frit has a pore size of 0.2 or 0.5 µm.

4. The method of claim 2, wherein said bed material is particulate and the particles have a diameter from 1 to 10 µm.

5. The method of claim 1, wherein said liquid chromatography is high performance liquid chromatography (HPLC).

6. The method of claim 1, wherein said releasing reagent is capable of releasing at least 99% of 25 OH-vitamin $D_3$ from the vitamin D binding protein.

7. The method of claim 1, wherein the vitamin D metabolite is 25 OH-vitamin $D_3$.

8. The method of claim 1, wherein the sample is blood serum or blood plasma.

9. A kit for measuring a vitamin D metabolite in a sample, the kit comprising a vitamin D releasing reagent and an isotope-labeled vitamin D metabolite, wherein said isotope-labeled vitamin D metabolite is present as a separate component or is contained within the vitamin D releasing reagent and wherein said releasing reagent comprises a salt having a quaternary N-heterocycle cation.

* * * * *